(12) United States Patent
Wasserman

(10) Patent No.: US 6,369,194 B1
(45) Date of Patent: Apr. 9, 2002

(54) VICINYL TRICARBONYL COMPOUNDS AND COMBINATORIAL LIBRARIES CONTAINING SAME

(75) Inventor: Harry H. Wasserman, Hamden, CT (US)

(73) Assignee: Yale University, New Haven, CT (US)

(*) Notice: Subject to any disclaimer, the term of this patent is extended or adjusted under 35 U.S.C. 154(b) by 0 days.

(21) Appl. No.: 09/188,478

(22) Filed: Nov. 9, 1998

(51) Int. Cl.$^7$ .............................. C07K 1/02; C07C 69/44
(52) U.S. Cl. .................. 530/324; 530/300; 530/333; 530/338; 530/340; 435/7.1; 435/536; 560/19; 560/20; 560/21; 560/22; 560/23; 560/38; 560/39; 560/42; 560/43; 560/45; 560/51; 560/53; 560/116; 560/117; 560/118; 560/119; 560/120; 560/121; 560/122; 560/123; 560/124; 560/125; 560/126; 560/150; 560/169; 560/170; 560/174
(58) Field of Search .................... 560/174, 19–23, 560/38–39, 42, 43, 45, 51, 53, 116–126, 156, 169, 170; 530/340, 324, 338, 333, 360; 435/7.1, 536

(56) References Cited

U.S. PATENT DOCUMENTS 4,929,751 A * 5/1990 Wasserman ............... 560/174
5,834,588 A * 11/1998 Wasserman ............... 530/340

OTHER PUBLICATIONS

Wasserman et al., Bioorg. & Med. Chem. Lett., vol. 5, No. 24, pp. 3033–3038, 1995.*
Wasserman et al. Tetrahedron Lett., vol. 36, No. 37, pp. 6785–6788, 1995.*
Conde–Frieboes et al., JACS, 118, pp. 5519–5525, 1996.*
J. Organ. Chem. 1994, 59, 4364–4366, entitled (Cyanomethylene) phosphoranes as Novel Carbonyl1, 1–Dipole Synthons: An Efficient Synthesis of a–Keto Acids, Esters, and Amides.
J. Organ. Chem. 1993, 58, 4785–4787, entitled Synthesis and Evaluation of Peptidyl Vicinal Tricarbonyl Monohydrates as Inhibitors of Hydrolytic Enzymes.

* cited by examiner

Primary Examiner—Bennett Celsa
(74) Attorney, Agent, or Firm—Pennie & Edmonds LLP

(57) ABSTRACT

The invention relates to compounds of formula

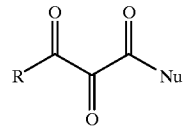

where R is a structural diversity element selected from the group consisting of alkyl, cycloalkyl, aryl, heteroaryl, peptidyl, heteroatom-substituted alkyl, cycloalkyl, and amines; and Nu is a structural diversity element derived from a nucleophile, NuH, selected from the group consisting of amines, amino acids, peptide, water, hydrogen sulfide, alcohols, and thiols. The invention also relates to arrays and combinatorial libraries of such compounds, and to a method of preparing such compounds.

22 Claims, No Drawings

VICINYL TRICARBONYL COMPOUNDS AND COMBINATORIAL LIBRARIES CONTAINING SAME

FIELD OF THE INVENTION

The present invention relates to tricarbonyl compounds, and, in particular, to $\alpha,\beta$-diketo acids, esters, and amides and a method of synthesis thereof. In addition, the present invention also relates to a method for the modular development of tricarbonyl compounds that have selected properties for a particular application. The $\alpha,\beta$-diketo compounds are developed from (cyanomethylene)phosphoranes, carboxylic acids, and nucleophiles that include selected substituent groups that provide the desired properties in the $\alpha,\beta$-diketo compounds. The iterative application of the method of the invention facilitates the synthesis of compounds having selected properties to meet the requirements of the particular application.

BACKGROUND OF THE INVENTION

The discovery of new molecules has traditionally focused in two broad areas, biologically active chemical compounds, which are used as drugs for the treatment of life-threatening diseases, and new materials, which are used in commercial, and, especially, in high technological applications. In both areas, the strategy used to discover new compounds has involved two basic operations: the more or less random choice of a molecular candidate, prepared either via chemical synthesis or isolated from natural sources, and the testing of the molecular candidate for useful properties. This discovery cycle is repeated indefinitely until a molecule of a compound possessing the desirable property, i.e., a "lead molecule", is isolated or synthesized. This "lead molecule" discovery process is inherently ad hoc in nature, and is time-consuming, laborious, unpredictable and costly.

Once a candidate lead molecule has been determined for a particular application, the synthetic chemist must subsequently find ways to synthesize structural variants of the lead molecule to optimize its properties for the application. In the case where the lead molecule is a synthesized organic species or a natural product, the chemist is usually limited to certain structural and synthetic reaction schemes. These schemes are dictated largely by the structural composition of the lead molecule and by the specific requirements of the application. For example, in cases where the lead molecule possesses a functionally important aromatic ring, various electrophilic and nucleophilic substitutions may be carried out on the ring to produce variants. However, each such case must be approached as a specific independent design and synthesis problem, starting each time from the beginning, because of the lack of availability of an appropriate chemistry to simply alter the structure of the lead compound to produce the variant.

Recently, some attempts have been made to modularize certain synthetic organic reaction schemes to facilitate modification and transformation of a lead or base compound. See, e.g., 1993 Proc. Natl. Acad. Sci. USA, 90, 6909. However, the molecules that can be produced by such attempts are extremely limited in their achievable diversity, and are still bounded by factors dictated by the choice of specific structural themes. In the case where the lead molecule is a naturally occurring, biological molecule, such as a peptide, a protein, an oligonucleotide or a carbohydrate, simple synthetic point-modifications to the lead molecule to produce variants are quite difficult to achieve.

A brief account of the strategies and tactics used in the discovery of new molecules is described below. Although the emphasis of the discussion is on molecules of biological interest, the technical problems encountered in the discovery of biologically active molecules is also illustrative of the problems encountered in the discovery of molecules that can serve as building blocks for the development of new tools and materials for a variety of high technological applications. Furthermore, as discussed below, these problems are also illustrative of the problems encountered in the development of fabricated structures and materials for high technological applications.

Modern theories of biological activity state that biological activities and, therefore, physiological states are the result of molecular recognition events. For example, nucleotides can form complementary base pairs so that complementary single-stranded molecules hybridize, resulting in double- or triple-helical structures that appear to be involved in regulation of gene expression. In another example, a biologically active molecule, referred to as a ligand, binds with another molecule, usually a macromolecule referred to as ligand-acceptor (e.g., a receptor, an enzyme, etc.), and this binding elicits a chain of molecular events which ultimately gives rise to a physiological state, e.g., normal cell growth and differentiation, abnormal cell growth leading to carcinogenesis, blood-pressure regulation, nerve-impulse generation and propagation, etc. The binding between ligand and ligand-acceptor is geometrically characteristic and extraordinarily specific, involving appropriate three-dimensional structural arrangements and chemical interactions.

A currently favored strategy for the development of agents which can be used to treat diseases involves the discovery of forms of ligands of biological receptors, enzymes, or related macromolecules, which mimic such ligands and either boost, i.e., agonize, or suppress, i.e., antagonize, the activity of the ligand. The discovery of such desirable ligand forms has traditionally been carried out either by random screening of molecules (produced through chemical synthesis or isolated from natural sources), or by using a so-called "rational" approach involving identification of a lead-structure, usually the structure of the native ligand, and optimization of its properties through numerous cycles of structural redesign and biological testing. Since most useful drugs have been discovered not through the "rational" approach, but through the screening of randomly chosen compounds, a hybrid approach to drug discovery has recently emerged which is based on the use of combinatorial chemistry to construct huge libraries of randomly-built chemical structures which are screened for specific biological activities. Brenner et al., 1992, Proc. Natl. Acad. Sci. USA, 89, 5381.

Most lead-structures which have been used in the "rational" drug design approach are native polypeptide ligands of receptors or enzymes. The majority of polypeptide ligands, especially the small ones, are relatively unstable in physiological fluids, due to the tendency of the peptide bond to undergo facile hydrolysis in acidic media or in the presence of peptidases. Thus, such ligands are decisively inferior in a pharmacokinetic sense to non-peptidic compounds, and are not favored as drugs. An additional limitation of small peptides as drugs is their low affinity for ligand acceptors. This phenomenon is in sharp contrast to the affinity demonstrated by large, folded polypeptides, e.g., proteins, for specific acceptors, such as receptors or enzymes, which often exist in the sub-nanomolar concentration range. For peptides to become effective drugs, they must be transformed into non-peptidic organic structures, i.e., peptide mimetics, which bind tightly, preferably in the nanomolar range, and can withstand the chemical and biochemical rigors of coexistence with biological tissues and fluids.

Despite numerous incremental advances in the art of peptidomimetic design, no general solution to the problem of converting a polypeptide-ligand structure to a peptidomimetic has been defined. At present, "rational" peptidomimetic design is done on an ad hoc basis. Using numerous redesign/synthesis/screening cycles, peptidic ligands belonging to a certain biochemical class have been converted by groups of organic chemists and pharmacologists to specific peptidomimetics. However, in the majority of cases, results in one biochemical area, such as, peptidase inhibitor design using the enzyme substrate as a lead, cannot be transferred for use in another area, such as, tyrosine-kinase inhibitor design using the kinase substrate as a lead.

In many cases, the peptidomimetics that result from a peptide structural lead using the "rational" approach comprise unnatural alpha-amino acids. Many of these mimetics exhibit several of the troublesome features of native peptides, which also comprise alpha-amino acids, and are, thus, not favored for use as drugs. Recently, fundamental research on the use of non-peptidic scaffolds, such as steroidal or sugar structures, to anchor specific receptor-binding groups in fixed geometric relationships have been described. See, e.g., Hirschmann et al., 1992 J. Am. Chem. Soc., 114, 9699–9701, and Hirschmann et al., 1992 J. Am. Chem. Soc., 114, 9217–9218. However, the success of this approach remains to be seen.

In an attempt to accelerate the identification of lead-structures, and also the identification of useful drug candidates through screening of randomly chosen compounds, researchers have developed automated methods for the generation of large combinatorial libraries of peptides and certain types of peptide mimetics, e.g., "peptoids", which are screened for a desirable biological activity. For example, the method of Geysen, 1984 Proc. Natl. Acad. Sci. USA, 81, 3998, employs a modification of the Merrifield peptide synthesis, wherein the C-terminal amino acid residues of the peptides to be synthesized are linked to solid-support particles shaped as polyethylene pins. These pins are treated individually or collectively in sequence to introduce additional amino-acid residues forming the desired peptides. The peptides are then screened for activity without removing them from the pins.

Houghton, 1985, Proc. Natl. Acad. Sci. USA, 82, 5131, and U.S. Pat. No. 4,631,211, utilizes individual polyethylene bags ("tea bags") containing C-terminal amino acids bound to a solid support. These are mixed and coupled with the requisite amino acids using solid phase synthesis techniques. The peptides produced are then recovered and tested individually.

Fodor et al., 1991, Science, 251, 767, described light-directed, spatially addressable parallel-peptide synthesis on a silicon wafer to generate large arrays of addressable peptides that can be directly tested for binding to biological targets. These workers have also developed recombinant DNA/genetic engineering methods for expressing huge peptide libraries on the surface of phages. Cwirla et al., 1990, Proc. Natl. Acad. Sci. USA, 87, 6378.

In another combinatorial approach, V. D. Huebner and D. V. Santi (U.S. Pat. No. 5,182,366) utilized functionalized polystyrene beads divided into portions each of which was acylated with a desired amino acid; the bead portions were mixed together, then divided into portions each of which was re-subjected to acylation with a second desirable amino acid producing dipeptides, using the techniques of solid phase peptide synthesis. By using this synthetic scheme, exponentially increasing numbers of peptides were produced in uniform amounts which were then separately screened for a biological activity of interest. Another method of producing libraries of organic compounds based on dipeptides, hydantoins and benzodiazepines using a polystyrene based solid support is described by DeWitt et al. 1993, Proc. Natl. Acad. Sci. USA, 90, 6909.

Bunin et al., 1992, J. Am. Chem. Soc., 114, 10997, describe a method for the combinatorial synthesis of large libraries of peptides. According to Bunin, 2-amino benzophenones are attached to a polystyrene solid support and converted into various 1,4 benzodiazepine derivatives, which can then be screened for specific receptor or enzyme activity.

Zuckerman et al., 1992, Int. J. Peptide Protein Res. 91, 1 and 1993, Structural Biology, 3, 580, also have developed similar methods for the synthesis of peptide libraries and applied these methods to the automation of a modular synthetic chemistry for the production of libraries of, for example, N-alkyl glycine peptide derivatives, called 44 peptoids", which are screened for activity against a variety of biochemical targets. See also, Symon et al., 1992, Proc. Natl. Acad. Sci. USA, 89, 9367. Encoded combinatorial chemical syntheses have been described recently. Brenner et al., 1992, Proc. Natl. Acad. Sci. USA, 89, 5381.

The focus of these structural diversity activities on peptide synthesis chemistry is a direct result of the fact that the ability to generate structural diversity requires, as its starting point, the access to practical stepwise sequential synthesis chemistries that allow the incorporation of varied structural elements with orthogonal reactivities. To date, these have only been worked out for the Merrifield synthesis of peptides and the Carruthers synthesis of oligonucleotides. Thus, there remains a need for an improved method for the structure-directed generation and screening of organic compounds to determine which may be suitable in a particular application.

One group of compounds that allow the incorporation of varied structural elements are $\alpha$-keto acids, esters, and amides. The $\alpha$-keto esters and amides are known to be potent inhibitors of proteolytic enzymes, such as serine and cysteine protease, as well as showing inhibition of leukotriene $A_4$ hydrolase and chymase, Wasserman et al., (Cyanomethylene)phosphoranes as Novel Carbonyl 1,1-Dipole Synthons: An Efficient Synthesis of $\alpha$-Keto Acids, Esters, and Amides, J. Org. Chem 1994, 59, 4364–4366 ("Wasserman 1994"). The biological activity of these compounds is believed to be the result of the presence of the electron-deficient $\alpha$-keto group, which is similar in reactivity to the carbonyl group of $\alpha$-fluorinated inhibitors and the $\alpha$- and $\beta$-carbonyl groups in vicinyl tricarbonyls.

Vicinyl tricarbonyls include $\alpha,\beta$-diketo amides, which are more reactive than $\alpha$-keto amides, and are found in a number of biologically active, naturally occurring peptide analogues, such as the immunosuppressants FK-506, rapamycin, and the elastase inhibitors YM-47141 and YM-47142. Because of their biological activity and potential as immunosuppressants and inhibitors, a method for the synthesis of $\alpha,\beta$-diketo acids, esters and amides is highly desirable.

Wasserman 1994 teaches a method for the synthesis of $\alpha$-keto acids, esters, and amides. A ylide, (cyanomethylene) triphenylphosphorane, undergoes a coupling reaction with a carboxylic acid to form a cyano keto phosphorane. The cyano keto phosphorane is readily oxidized to form a highly electrophilic vicinal diketo nitrile that can be trapped at low temperature by reaction with nucleophiles to form a transient cyanohydrin intermediate. The cyanohydrin readily undergoes elimination of hydrogen cyanide to form an α-keto acid, ester or amide. Whether an α-keto acid ester or amide is formed is determined by the choice of nucleophile. Structural diversity is obtained by the appropriate choice of the carboxylic acid and nucleophile.

Wasserman et al., 1993 Synthesis and Evaluation of Peptidyl Vicinal Tricarbonyl Monohydrates as Inhibitors of Hydrolytic Enzymes, J. Org. Chem., 58, 4785–4787 ("Wasserman 1993"), disclose peptidyl vicinal tricarbonyls, prepared from N-protected di- and tripeptides by reaction of carboxylic acid residues with ylides, followed by oxidation. The peptide vicinal tricarbonyls have been shown to be potent inhibitors of serine protease.

However, there is no teaching in the prior art of a method for the synthesis of α,β-diketo acids, esters, or amides from α-keto acids. The present invention provides such a method.

SUMMARY OF THE INVENTION

The present invention relates to a method for the synthesis of vicinyl tricarbonyl compounds, and, in particular, α,β-diketo acids, esters, and amides, i.e., vicinyl tricarbonyl compounds of formula

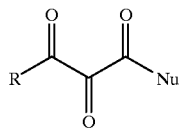

where R is a structural diversity element selected from the group consisting of alkyl, cycloalkyl, aryl, heteroaryl, peptidyl, heteroatom-substituted alkyl, cycloalkyl, alcohols, and amines; and Nu is a structural diversity element derived from a nucleophile, NuH, selected from the group consisting of amines, amino acids, peptides, water, hydrogen sulfide, alcohols, and thiols.

The method of the invention comprises reacting an α-keto acid with a ylide, preferably a (cyanomethylene) phosphorane, such as a triphenylphosphorane, under sufficient reaction conditions (i.e., pressure, temperature, and time, and preferably in the presence of 1-(3-dimethylaminopropyl)-3-ethylcarbodiimide hydrochloride) to form a cyano diketo phosphorane, oxidizing the cyano diketo phosphorane, preferably with ozone, forming a cyano tricarbonyl and reacting the cyano tricarbonyl with a nucleophile to form the α,β-diketo acid, ester, or amide. Preferably, the nucleophile is an amine, amino acid, peptide, hydrazine, water, hydrogen sulfide, alcohol, or thiol. Typically, the cyano diketo phosphorane is oxidized with ozone in $CH_2Cl_2$ at a temperature of less than about −60° C., preferably about −78° C., and the cyano tricarbonyl is reacted with the nucleophile for about 2 to about 60 minutes at a first temperature of less than about −60° C., preferably about −78° C., followed by from about 30 minutes to about 4 hours at a second temperature of less than about 5° C., preferably about 0° C.

The α-keto acid is typically formed by reacting a ylide, again, preferably a (cyanomethylene)phosphorane, such as a triphenylphosphorane, under sufficient reaction conditions with a carboxylic acid or acid chloride to form the corresponding cyano keto phosphorane, oxidizing the cyano keto phosphorane, again, preferably with ozone, forming a vicinyl diketo nitrile; and trapping the vicinyl diketo nitrile with water, forming an α-keto acid. Preferably, the carboxylic acid contains a structural diversity element of an alkyl, cycloalkyl, aryl, heteroaryl, peptidyl, heteroatom-substituted alkyl, cycloalkyl, or amine group. The carboxylic acid can be an amino acid.

The nucleophile used to form α,β-diketo acid, ester, or amide of the invention may be an alcohol comprising from 1 to about 10 carbon atoms, an amino acid selected from the group consisting of tryptophan, arginine, histidine, glutamic acid, glutamine, aspartic acid, leucine, threonine, proline, alanine, tyrosine, carbamido cysteine, phenylalanine, methionine, lysine, asparagine, isoleucine, cysteine, valine, serine, and glycine, an amine comprising at least one alkyl or cycloalkyl group comprising 1 to about 10 carbon atoms, or a heterocyclic ring compound comprising at least one nitrogen atom and from 3 to about 10 carbon atoms in the ring.

Arrays may be formed by making compounds according to the invention, and spatially arranging a plurality of such compounds to form the array. Typically, an m×p array of q α,β-diketo molecules or an m×p array of compartments is formed, where each compartment contains an α,β-diketo compound, and where m and p are integers representing the number of rows and columns in the array, and q is an integer in the range of from 1 to the product of m multiplied by p, and represents the number of different compounds in the array. The product of m multiplied by p is typically at least about 25, but is preferably at least about 3,000, and may exceed 10,000. The array may then be used in a combinatorial library of compounds, comprising r different α,β-diketo compounds, wherein r is an integer greater than 1, typically greater than 25, and may exceed 100,000.

The invention also relates to a combinatorial library of compounds, comprising r different compounds of formula

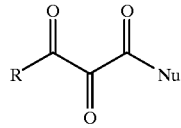

wherein R is a structural diversity element selected from the group consisting of alkyl, cycloalkyl, aryl, heteroaryl, peptidyl, heteroatom-substituted alkyl, heteroatom-substituted cycloalkyl, and amines; Nu is a structural diversity element derived from a nucleophile, NuH, by removal of a hydrogen atom, wherein NuH is selected from the group consisting of amines, amino acids, peptide, water, hydrogen sulfide, alcohols, and thiols; and r is an integer of 2 to 96.

Preferably, r is an integer greater than 25, and at least one of R or Nu is derived from an amino acid by removal of a hydrogen atom, where Nu may be an amino acid selected from the group consisting of tryptophan, arginine, histidine, glutamic acid, glutamine, aspartic acid, leucine, threonine, proline, alanine, tyrosine, carbamido cysteine, phenylalanine, methionine, lysine, asparagine, isoleucine, cysteine, valine, serine, and glycine, and R may be an amino acid selected from the group consisting of arginine, glutamic acid, glutamine, aspartic acid, leucine, threonine, proline, alanine, tyrosine, phenylalanine, lysine, asparagine, isoleucine, valine, serine, and glycine.

In an alternate embodiment, the invention relates to a method for making an array of compounds. The method comprises preparing compounds according to the following method:

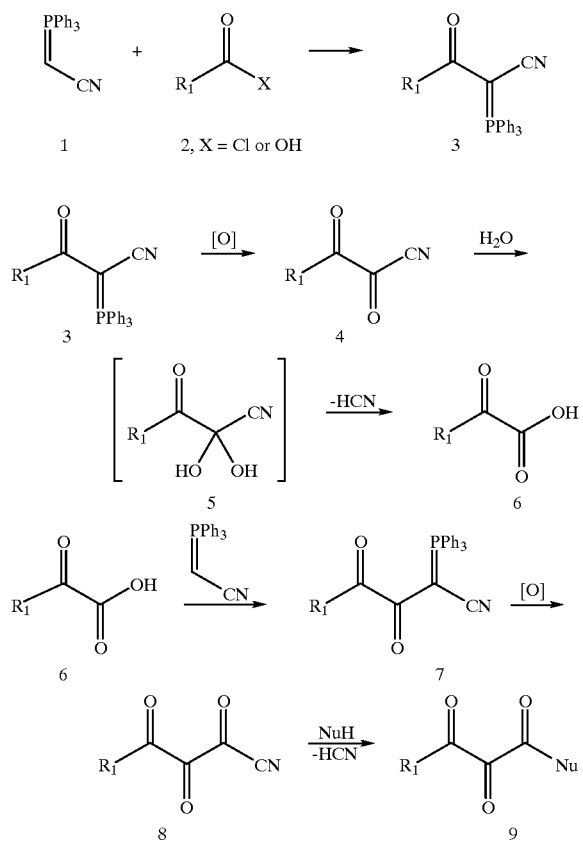

diketo acids, esters, and amides, and to the formation of combinatorial libraries containing α,β-diketo compounds.

The vicinyl tricarbonyl compounds of the invention are synthesized from α-keto acids produced in accordance with the method disclosed by Wasserman 1994 and in copending U.S. patent application Ser. No. 08/503,070, the content of which is incorporated in its entirety by reference. The α-keto acid is subjected to a coupling reaction with a (cyanomethylene)phosphorane, such as a triphenylphosphorane, in the presence of 1-(3-dimethylaminopropyl)-3-ethylcarbodiimide hydrochloride ("EDCI") to form a cyano diketo phosphorane. The cyano diketo phosphorane is then oxidized to form a highly electrophilic vicinyl triketo nitrile that is trapped with a nucleophile to form a cyanohydrin intermediate. The cyanohydrin then undergoes facile elimination of hydrogen cyanide to form an α,β-diketo acid, ester, or amide, depending on the nucleophile used.

More specifically, a (cyanomethylene)phosphorane, 1, a ylide, is made to undergo a coupling reaction with a carboxylic acid or acid chloride of formula 2 to form a cyano keto phosphorane of formula 3, as shown below.

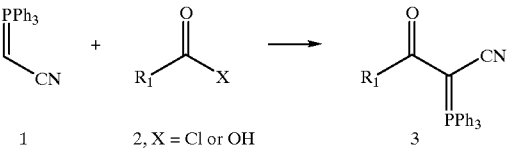

The cyano keto phosphorane, 3, is then oxidized, preferably with ozone ($O_3$) to form a vicinyl diketo nitrile, 4. Upon nucleophilic attack by water, the vicinyl diketo nitrile, 4, forms a cyanohydrin intermediate of formula 5. The cyanohydrin intermediate 5 readily eliminates hydrogen cyanide to form an α-keto acid, 6.

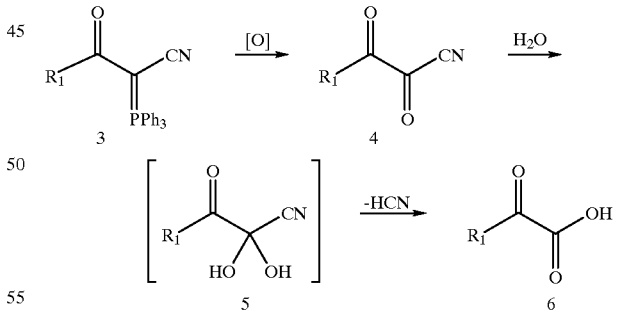

The α-keto acid, 6, is then converted to an α,β-diketo acid, ester, or amide by first making the α-keto acid, 6, undergo a second coupling reaction with a (cyanomethylene)phosphorane to form a cyano diketo phosphorane, 7, which is oxidized, preferably by ozone, to form a cyano tricarbonyl, 8. On reaction of the cyano tricarbonyl, 8, with a nucleophile of formula NuH, an intermediate is formed that readily eliminates hydrogen cyanide to form an α,β-diketo acid, ester, or amide.

wherein $R_1$ is a structural diversity element selected from the group consisting of alkyl, cycloalkyl, aryl, heteroaryl, peptidyl, heteroatom-substituted alkyl, cycloalkyl, and amines; and Nu is a structural diversity element derived from a nucleophile, NuH, by removal of a hydrogen atom, wherein NuH is selected from the group consisting of amines, amino acids, peptide, water, hydrogen sulfide, alcohols, and thiols; and spatially arranging a plurality of such compounds to form the array.

Preferably, $R_1$ is derived from an amino acid by removal of a hydrogen atom, where the amino acid is selected from the group consisting of arginine, glutamic acid, glutamine, aspartic acid, leucine, threonine, proline, alanine, tyrosine, phenylalanine, lysine, asparagine, isoleucine, valine, serine, and glycine, the oxidizing step is carried out with ozone, the nucleophile NuH is an alcohol, a thiol, an amine, an amino acid, a peptide, or hydrazine.

The invention also relates to a method for the synthesis of a triacyl diamide. The method of the invention comprises reacting a secondary amine with an alkyl oxalyl chloride to form an oxalyl ester, hydrolyzing the oxalyl ester in LiOH/THF to a carboxylic acid, reacting the carboxylic acid with a (cyanomethylene)phosphorane to form a cyano diketo phosphorane, oxidizing the cyano diketo phosphorane to produce a triacyl nitrile intermediate that is susceptible to attack by a nucleophile, and reacting the triacyl nitrile intermediate with a second amine, preferably a secondary amine to form the triacyl diamide.

DETAILED DESCRIPTION OF THE INVENTION

The present invention relates to a method for the synthesis of vicinyl tricarbonyl compounds, and, in particular, α,β-

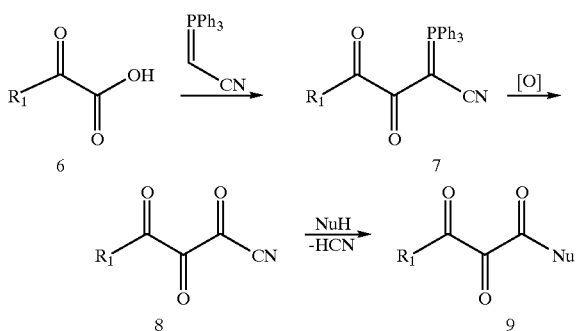

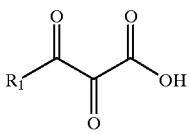

Whether the resulting α,β-diketo compound is an acid, ester, or amine depends on the nucleophile used. For example, where the nucleophile, NuH, is water, an α,β-diketo acid of formula I is formed.

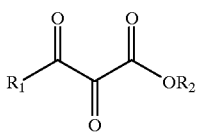

Similarly, where nucleophile NuH is an alcohol of formula $R_2OH$, an α,β-diketo ester of formula II is formed,

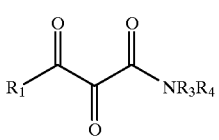

and where nucleophile NuH is an amine of formula $HNR_3R_4$, an α,β-diketo amide of formula III is formed.

Groups $R_1$, $R_2$, $R_3$, $R_4$, and Nu are structural diversity elements that are specifically chosen for the properties and structure that they provide to the resulting α,β-diketo compound. The R groups, $R_1$, $R_2$, $R_3$, and $R_4$, may be the same or different, and include, but are not limited to alkyl, cycloalkyl, substituted and unsubstituted aryl, heteroaryl, heteroatom-substituted alkyl and cycloalkyl, amidyl, peptidyl, and alkoxyl. Useful Nu groups are derived from nucleophiles of formula NuH that include, but are not limited to amines (including hydrazines and primary and secondary amines), amino acids, peptides, water, hydrogen sulfide, alcohols, thiols, and carbon-centered nucleophiles, such as indoles, enamines, enols, enolates, silyl enol ethers, ethers, cuprates and other metallated species. Useful peptides include peptides containing from 2 to about 50, preferably 2 to about 25 amino acids. Useful amino acids include, but are not limited to, tryptophan, arginine, histidine, glutamic acid, glutamine, aspartic acid, leucine, threonine, proline, alanine, tyrosine, carbamido cysteine, phenylalanine, methionine, lysine, asparagine, isoleucine, cysteine, valine, serine, and glycine.

As can be seen from the reaction scheme set forth above, in one embodiment, structural diversity element $R_1$ is determined by the selection of the carbonyl compound of formula 2 that undergoes the coupling reaction with the ylide, 1, to form cyano keto phosphorane, 3. Similarly, structural diversity elements $R_2$, $R_3$, $R_4$, and Nu are determined by the choice of the nucleophile selected to trap the cyano tricarbonyl, 8, which then eliminates hydrogen cyanide to form the desired α,β-diketo compound.

In an alternate embodiment, tricarbonyl derivatives can be formed by converting a secondary amine to an oxalyl ester, which is then hydrolyzed in LiOH/THF to the corresponding carboxylic acid. The carboxylic acid is then coupled with a (cyanomethylene)phosphorane for the oxidative incorporation of a third carbonyl group. The triacyl nitrile intermediate is then made to react with a nucleophile, as in the scheme described above, to form the desired α-β-diketo compound.

This process may be used to form novel triacyl diamides. A secondary amine, 10, is made to react with an ester-acid chloride of formula 11 to form an oxalyl ester, 12, which is hydrolyzed in LiOH/THF to the corresponding carboxylic acid, 13. The α-keto ester may be synthesized using the method described above for the synthesis of α-keto acids by using an alcohol of formula ROH as the nucleophile.

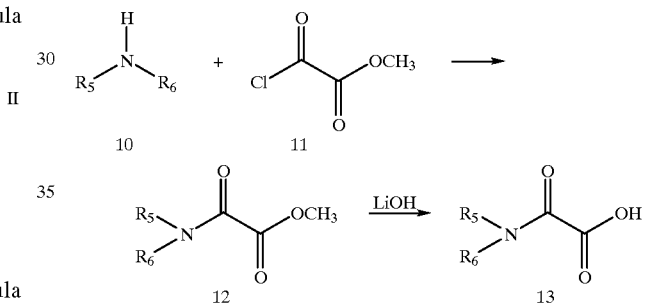

The carboxylic acid, 13, is then made to undergo the coupling reaction with a (cyanomethylene)phosphorane in EDCI, as described above, to form a cyano diketo phosphorane of formula 14, as shown below.

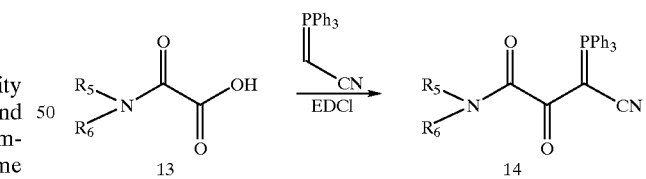

Oxidation of the cyano diketo phosphorane, 14, produces a triacyl nitrile intermediate, 15, that is susceptible to attack by a nucleophile.

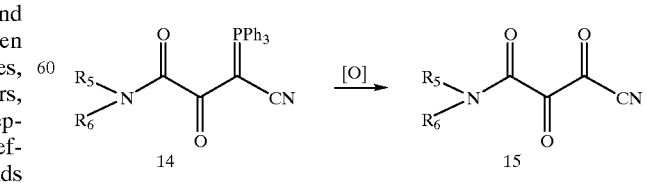

Where the nucleophile is a secondary amine, the resulting α-β-diketo compound is a triacyl diamide, 16. It has been discovered that the reaction of the triacyl nitrile, 15, with the nucleophile occurs at the α-carbonyl, leading to the formation of the tricarbonyl derivative, 16.

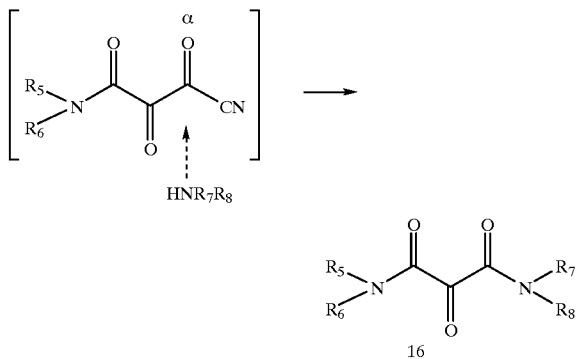

Prior to the present invention, it was believed that attack by the nucleophile could occur at the β-carbonyl, leading to the elimination of carbon monoxide and hydrogen cyanide, and the formation of an α-keto compound.

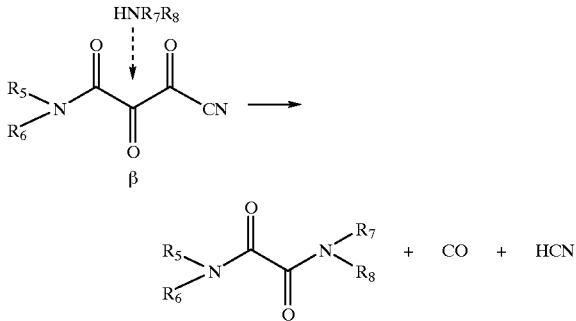

Although this result is obtained in certain cases that have geometric features that favor attack by the nucleophile at the β-carbonyl, the reaction typically occurs exclusively at the α-carbonyl. This is significant, because it is believed that the β-carbonyl should be more electrophilic than the α-carbonyl. Without being bound by theory, it is believed that the β-attack may be reversible, while the attack at the α-carbonyl results in the irreversible elimination of cyanide. Similar results are obtained with nucleophiles other than amines, e.g., alcohols and water, resulting in the formation of α,β-diketo esters and acids, as well as the triacyl amides formed where the nucleophile is an amide, as shown above.

The ability of these various reactions to be carried out in a stepwise sequential process using modules chosen in a structure-directed manner allows the production of structurally directed thematic diversity libraries, having, structural elements systematically varied around a basic motif.

Combinatorial libraries of α,β-diketo compounds may be synthesized by the modular development of α,β-diketo acids, esters, and amides that have selected properties. Once the library has been formed, the α,β-diketo compounds that make up the library may be screened to determine which compounds best meet the requirements of a particular application.

The present invention may be used to generate a number of different molecules for screening purposes by first forming an α,β-diketo compound as a base module having at least two structural diversity elements attached. By fixing one of the positions and structures of the structural diversity elements, and by varying at least one of the others, an array of different α,β-diketo molecules is easily generated. These molecules can then be screened to determine which are suitable for a particular application or target use. Once a suitable α,β-diketo compound is identified, it can be selected for generating a further array of molecules. This is done by modifying the particular structural diversity elements that are found to be suitable, or by combining the chosen structural diversity element with an expanded or different set of second compounds or elements. This process can be repeated as often as necessary to develop the optimum compound for the particular use.

The particular α,β-diketo base module chosen for use in accordance with the present invention is not critical, and can be any one of a wide variety of structures. Knowledge of the base modules can be represented in the form of combinatorial libraries.

From the foregoing, it is seen that various arrays of α,β-diketo molecules can be prepared. These arrays can be generated in any size desired to facilitate the screening of a large number of molecules at one time, and are preferably spatially arranged. For example, standard arrays having 96 compartments in an 8×12 array can be used, where any number of compartments in the array contain different molecules, while the other can contain controls or duplicate samples. Preferably, in an 8×12 array, 16 of the compartments contain controls and 80 compartments contain different samples. After an initial screening identifies α,β-diketo molecules having certain beneficial or desirable properties, a second tray containing, e.g., 20 samples of each of 4 different α,β-diketo molecules, again with 16 control samples, can be used to confirm the original results. The samples can be placed in columns of the same material, or a completely random array can be generated to have a completely blind analysis.

In view of these variations, one of ordinary skill in the art would understand that any m×p array of molecules can be generated, where m and p are integers, m being greater than zero, and p being greater than 1. There is no upper limit to m and p other than the capabilities of the testing or screening equipment. As noted above, an 8×12 array is typical, but q compounds can be tested from arrays where m or p is as high as 25 or more; q being an integer from 1 up to the total of m times p, and typically being between 2 and 96, although significantly larger arrays are contemplated. At this time, it is specifically preferred that m and p be integers of between 3 and 15, and that a few control molecules be included so that q is less than the product of m and p. However, this invention contemplates that use of any integer for m or p, with each integer or combination of m×p integers relied upon as representing a useful embodiment. Thus, q may be an integer equal to 1 up to the product of m multiplied by p.

As noted above, the α,β-diketo molecules used in the array would be generated from one or more of the α,β-diketo base molecules described herein. In this manner, combinatorial libraries of r different compounds, where r is any integer greater than 1, can be made. Typically, r will be greater than 5, preferably at least 25. As noted, r can be as high as 80 or 96 using available trays, or can even be any higher number using multiple or specifically designed trays. Although for convenience, linear arrays are described, the specific arrangement of the molecules and tray compartments can be circular, staggered or in any other configuration which can be analyzed by the testing or screening device used.

In one embodiment of the present invention at least two of the structural diversity elements, $R_1$, $R_2$, $R_3$, $R_4$, or Nu, are present, and one or more are reactive groups that are capable of further reactions to produce a base module. For example, the present invention is directed to structural diversity groups that may themselves be capable of further reaction to form base modules as described herein.

The determination of compounds that meet the requirements of a particular application involves a process, which comprises: a) the synthesis of an array of different α,β-diketo acids, esters, and amides, each containing substituent groups, selected to provide structural diversity to the elements of the array, and/or the reaction of α,β-diketo compounds with other reactive chemical species to alter or exchange substituent groups on the α,β-diketo compounds to produce an array, each element of which is a compound consisting of molecules having a selected set of substituent groups, such that each element of the array is a compound having selected properties that are determined by the selected substituent groups on the α,β-diketo acid, ester or amide molecules that make up the compound; and b) the screening of at least some of the elements of the array to determine which compounds in the array have properties that meet the requirements of a particular application.

The difference between the elements in the array is determined by the choice of structural diversity elements, i.e., the substituent group $R_1$, introduced into the α,β-diketo compound by carboxylic acid or acid chloride 2, and the substituent group Nu, introduced into the α,β-diketo compound by nucleophile NuH. As will be readily appreciated by one of ordinary skill in the art, the presence and the structure of structural diversity elements $R_2$, $R_3$, and $R_4$ are determined by the choice of nucleophile NuH. By the appropriate choice of $R_1$ and Nu, the resulting α,β-diketo compounds can be designed to have specific, pre-selected properties. For example, as described above, the choice of nucleophile determines whether the α,β-diketo compound will be an acid, an ester or an amide, where water provides an acid of formula I, an alcohol provides an ester of formula II, and an amine provides an amide of formula III. By varying both $R_1$ and Nu, an array of α,β-diketo compounds can be formed. Typically, each row of the array would have the same $R_1$ group with differing Nu groups, and each column would have the same Nu group with differing $R_1$ groups.

As used herein, the phrase alkyl means any branched or straight chain, substituted or unsubstituted acyclic carbon-containing compounds, including alkanes, alkenes and alkynes, typically containing up to about 30 carbon atoms. Examples of alkyl groups include lower alkyl, for example, methyl, ethyl, n-propyl, iso-propyl, n-butyl, iso-butyl or tert-butyl; upper alkyl, for example, octyl, nonyl, decyl, and the like; and lower alkylene, for example, ethylene, propylene, propyldiene, butylene, butyldiene, pentene, hexene, heptene, octene, norbornene, nonene, decene and the like. The ordinary skilled artisan is familiar with numerous linear and branched alkyl groups, which are within the scope of the present invention.

In addition, such alkyl groups may also contain various substituents in which one or more hydrogen atoms has been replaced by a functional group. Functional groups include, but are not limited to hydroxyl, amino, carboxyl, sulfonic amide, ester, ether, phosphates, thiol, nitro, silane, and halogen, i.e., fluorine, chlorine, bromine and iodine, to mention but a few. Substituted alkyl groups include, but are not limited to, alkoxy, e.g., methoxy, ethoxy, butoxy, and pentoxy, amino, e.g., dimethylamino, diethylamino, cyclopentylamino, benzylmethylamino, and dibenzylamino, amido, e.g., formamido, acetamido, and butanamido.

As used herein, cycloakyl means a substituted or unsubstituted cyclic carbon-containing compound, including, but not limited to, cyclopentyl, cyclohexyl, cycloheptyl, adamantyl, and the like. Such cyclic groups may also contain various substituents in which one or more hydrogen atoms has been replaced by a functional group. Such functional groups include those described above, and lower alkyl groups having from 1–28 carbon atoms. The cyclic groups of the invention may further comprise at least one heteroatom, typically a nitrogen forming a cyclic secondary amine, typically containing up to about 10 carbon atoms. Heterocyclic ring compounds containing more than one heteroatom are also useful in the invention.

As used herein, aryl groups means a substituted or unsubstituted hydrocarbon ring, bearing, a system of conjugated double bonds, comprising 4n+2π-bond electrons, where n is an integer greater than or equal to 0. Examples of aryl groups include, but are not limited to, phenyl, naphthyl, anisyl, toluyl, xylenyl and the like. According to the present invention, aryl also includes aryloxy, aralkyl, aralkyloxy and heteroaryl groups, e.g, pyrimidine, morpholine, piperazine, piperidine, benzoic acid, toluene or thiophene and the like. These aryl groups may be substituted with any number of a variety of functional groups. In addition to the functional groups described above in connection with substituted alkyl groups and carbocyclic groups, functional groups on the aryl groups can be nitro groups.

As mentioned above, these structural moieties can also be any combination of alkyl, carbocyclic or, aryl, groups, for example, 1-cyclohexylpropyl, benzylcyclohexylmethyl, 2-cyclohexylpropyl, 2,2-methylcyclohexylpropyl, 2,2-methylphenylpropyl, 2,2-methylphenylbutyl, and the like.

The following non-limiting examples are merely illustrative of the preferred embodiments of the present invention, and are not to be construed as limiting the invention, the scope of which is defined by the appended claims.

EXAMPLES

A series of α,β-diketo compounds was produced by first forming an α-cyano tricarbonyl using the synthetic method of the invention to form a diketo cyano ylide. The diketo cyano ylide was oxidized, and the resulting α-cyano tricarbonyl was coupled with various nucleophiles under mild conditions, as follows:

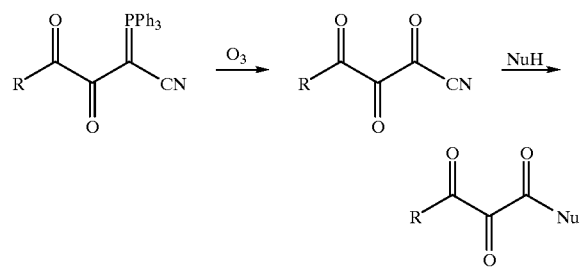

The oxidation step was performed with ozone in $CH_2Cl_2$ at –78° C. for 10 minutes. Reaction with the nucleophile was conducted for 30 minutes at –78° C., followed by 2 hours at 0° C. The results are provided in Table 1.

TABLE 1

| R(eq)* | NuH | Tricarbonyl | Yield %** |
|---|---|---|---|
| 1-piperidinyl (1.0) | pyrrolidine-2-carboxylic acid butyl ester (HN, BuO₂C) | piperidinyl-C(O)-C(O)-C(O)-pyrrolidinyl-CO₂Bu | 42 |
| 1-piperidinyl (1.5) | pyrrolidine-2-carboxylic acid tert-butyl ester (HN, Bu^tO₂C) | piperidinyl-C(O)-C(O)-C(O)-pyrrolidinyl-CO₂Bu^t | 89 |
| 1-piperidinyl (1.5) | pyrrolidine (HN) | piperidinyl-C(O)-C(O)-C(O)-pyrrolidinyl-CO₂Bu | 51 |
| 1-piperidinyl (1.5) | piperidine (HN) | piperidinyl-C(O)-C(O)-C(O)-piperidinyl | 64 |
| 1-piperidinyl (1.5) | 4-benzylpiperidine (HN-CH₂Ph) | piperidinyl-C(O)-C(O)-C(O)-(4-benzylpiperidinyl) | 58 |
| 1-piperidinyl (1.5) | HNCH₂Ph / CH₃ | piperidinyl-C(O)-C(O)-C(O)-N(CH₃)CH₂Ph | 64 |
| 1-piperidinyl (1.5) | 2-(cyclohex-1-enyl)ethylamine (NH₂) | piperidinyl-C(O)-C(O)-C(O)-NH-CH₂CH₂-cyclohexenyl | 31 |
| 1-piperidinyl (1.5) | 1-(1,3-benzodioxol-5-ylmethyl)piperazine (HN) | piperidinyl-C(O)-C(O)-C(O)-piperazinyl-CH₂-(1,3-benzodioxol-5-yl) | 85 |

TABLE 1-continued

| R(eq)* | NuH | Tricarbonyl | Yield %** |
|---|---|---|---|
| 1-piperidinyl (3.0) | piperazine | bis-piperidinyl tetracarbonyl piperazine derivative | 44 |
| 1-piperidinyl | CH₃OH | piperidinyl tricarbonyl methyl ester | 40 |
| 1-piperidinyl (2.0) | N-methylindole | 3-(N-methylindolyl) piperidinyl tricarbonyl | 52 |
| 1-pyrrolidinyl (2.0) | piperidine | pyrrolidinyl piperidinyl tricarbonyl | 46 |
| phenyl (2.0) | piperidine | phenyl piperidinyl tricarbonyl | 38 |
| | | phenyl piperidinyl dicarbonyl | 13 |

*Equivalents of diketo cyano ylide per equivalent of nucleophile.
**Yield based on amount of nucleophile.

While it is apparent that the invention disclosed herein is well calculated to fulfill the objects stated above, it will be appreciated that numerous modifications and embodiments may be devised by those skilled in the art. Therefore, it is intended that the appended claims cover all such modifications and embodiments that fall within the true spirit and scope of the present invention.

I claim:

1. A method for preparing a vicinyl tricarbonyl compound of the general formula:

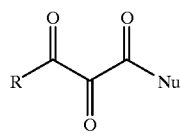

where R is a structural diversity element selected from the group consisting of alkyl, cycloalkyl, aryl, heteroaryl, peptidyl, heteroatom-substituted alkyl, cycloalkyl, alcohols, and amines; and Nu is a structural diversity element derived from a nucleophile, NuH, by removal of a H atom selected from the group consisting of amines, amino acids, peptides, water, hydrogen sulfide, alcohols, and thiols, which comprises:

reacting an α-keto acid or an acid chloride of an α-keto acid with a ylide, wherein said ylide is selected from (cyanomethylene)phosphoranes and triphenyl phosphoranes, to form a cyano diketo phosphorane;

oxidizing the cyano diketo phosphorane to form a cyano tricarbonyl; and reacting the cyano tricarbonyl with a nucleophile, NuH, as described above, to form said vicinyl tricarbonyl compound.

2. The method of claim 1, wherein the vicinyl tricarbonyl compound formed is an α,β-diketo acid, ester, or amide.

3. The method of claim 1, wherein the nucleophile is a compound having a formula selected from the group consisting of:

4. The method of claim 1, wherein the cyano diketo phosphorane is oxidized with ozone.

5. The method of claim 1, further comprising
reacting the α-keto acid with the ylide in the presence of 1-(3-dimethylaminopropyl)-3-ethylcarbodiimide hydrochloride;
oxidizing the cyano diketo phosphorane with ozone in $CH_2Cl_2$ at a temperature of less than about −60° C.; and
reacting the cyano tricarbonyl with the nucleophile for about 2 to about 60 minutes at a first temperature of less than about −60° C., followed by from about 30 minutes to about 4 hours at a second temperature of less than about 5° C.

6. The method of claim 5, wherein the cyano diketo phosphorane is oxidized at a temperature of about −78° C., and the cyano tricarbonyl is first reacted with the nucleophile at a temperature of about −78° C., and then reacted with the nucleophile at a temperature of about 0° C.

7. The method of claim 1, further comprising first forming the α-keto acid by reacting a second ylide with a carboxylic acid or acid chloride to form a cyano diketo phosphorane;
oxidizing the cyano keto phosphorane, to form a vicinyl diketo nitrile; and
trapping the vicinyl diketo nitrile with water to form an α-keto acid.

8. The method of claim 7, wherein the second ylide is a (cyanomethylene)phosphorane.

9. The method of claim 8, wherein the ylide is a triphenylphosphorane.

10. The method of claim 7, wherein the cyano diketo phosphorane is oxidized with ozone.

11. The method of claim 1 which further comprises preparing a plurality of different vicinyl tricarbonyl compounds and forming an m×p array of q different vicinyl tricarbonyl compounds, wherein m and p are integers, and q is an integer in the range of from 2 to m multiplied by p.

12. The method of claim 11, wherein m multiplied by p is a least about 3,000.

13. The method of claim 12, wherein m multiplied by p is at least about 10,000.

14. The method of claim 11, further comprising providing m×p compartments, with each compartment containing one of the q compounds.

15. The method of claim 11, wherein at least one of R or Nu is derived from an amino acid by removal of a hydrogen atom, where the amino acid is selected from the group consisting of tryptophan, arginine, histidine, glutamic acid, glutamine, aspartic acid, leucine, threonine, proline, alanine, tyrosine, carbamido cysteine, phenylalanine, methionine, lysine, asparagine, isoleucine, cysteine, valine, serine, and glycine.

16. The method of claim 11, wherein the m×p array includes q compounds of formula:

wherein
R is a structural diversity element selected from the group consisting of alkyl, cycloalkyl, aryl, heteroaryl, peptidyl, heteroatom-substituted alkyl, heteroatom-substituted cycloalkyl, and amines; and Nu is a structural diversity element derived from a nucleophile, NuH, by removal of a hydrogen atom, wherein NuH is selected from the group consisting of amines, amino acids, peptide, water, hydrogen sulfide, alcohols, and thiols.

17. The method of claim 16, wherein m multiplied by p is a least about 3,000.

18. The method of claim 17, wherein m multiplied by p is at least about 10,000.

19. The method of claim 18, further comprising providing m×p compartments, with each compartment containing one of the q compounds.

20. The method of claim 16, wherein at least one of R or Nu is derived from an amino acid by removal of a hydrogen atom, where, when R is an amino acid, R is selected from the group consisting of arginine, glutamic acid, glutamine, aspartic acid, leucine, threonine, proline, alanine, tyrosine, phenylalanine, lysine, asparagine, isoleucine, valine, serine, and glycine, and, when Nu is an amino acid, Nu is selected from the group consisting of tryptophan, arginine, histidine, glutamic acid, glutamine, aspartic acid, leucine, threonine, proline, alanine, tyrosine, carbamido cysteine, phenylalanine, methionine, lysine, asparagine, isoleucine, cysteine, valine, serine, and glycine.

21. The method of claim 1 which further comprises preparing a plurality of different vicinyl tricarbonyl compounds and forming a combinatorial library of r different vicinyl tricarbonyl compounds of formula:

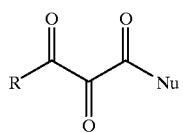

wherein

R is a structural diversity element selected from the group consisting of alkyl, cycloalkyl, aryl, heteroaryl, peptidyl, heteroatom-substituted alkyl, heteroatom-substituted cycloalkyl, and amines;

Nu is a structural diversity element derived from a nucleophile, NuH, by removal of a hydrogen atom, wherein NuH is selected from the group consisting of amines, amino acids, peptide, water, hydrogen sulfide, alcohols, and thiols; and r is an integer of at least 2.

22. The method of claim 21, wherein at least one of R or Nu is derived from an amino acid by removal of a hydrogen atom, where, when R is an amino acid, R is selected from the group consisting of arginine, glutamic acid, glutamine, aspartic acid, leucine, threonine, proline, alanine, tyrosine, phenylalanine, lysine, asparagine, isoleucine, valine, serine, and glycine, and, when Nu is an amino acid, Nu is selected from the group consisting of tryptophan, arginine, histidine, glutamic acid, glutamine, aspartic acid, leucine, threonine, proline, alanine, tyrosine, carbamido cysteine, phenylalanine, methionine, lysine, asparagine, isoleucine, cysteine, valine, serine, and glycine.

* * * * *

UNITED STATES PATENT AND TRADEMARK OFFICE
CERTIFICATE OF CORRECTION

PATENT NO. : 6,369,194 B1  Page 1 of 1
DATED : April 28, 2002
INVENTOR(S) : Harry H. Wasserman It is certified that error appears in the above-identified patent and that said Letters Patent is hereby corrected as shown below:

Column 1,
Line 4, insert:
-- This invention was made with government support under Grant #CHE 9307667 awarded by the National Institutes of Health (NIH). The government has certain rights in the invention. --

Signed and Sealed this

Twelfth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO.    : 6,369,194 B1                                           Page 1 of 1
DATED         : April 9, 2002
INVENTOR(S)   : Harry H. Wasserman It is certified that error appears in the above-identified patent and that said Letters Patent is hereby corrected as shown below:

<u>Column 1,</u>
Line 4, insert:
-- This invention was made with government support under Grant No. CHE 9307667 awarded by The National Science Foundation (NSF) and Grant No. GM 13854 awarded by the National Institutes of Health (NIH). The government has certain rights in the invention. --

Signed and Sealed this

Twenty-fifth Day of November, 2003

JAMES E. ROGAN
*Director of the United States Patent and Trademark Office*